United States Patent [19]

Salka et al.

[11] Patent Number: 5,514,369
[45] Date of Patent: May 7, 1996

[54] MILD SHAMPOO COMPOSITION

[75] Inventors: Barry A. Salka, Fair Lawn; Bruce W. Gesslein, Brick, both of N.J.; Robert M. Jablonski, Brooklyn, N.Y.

[73] Assignee: Henkel Corporation, Plymouth Meeting, Pa.

[21] Appl. No.: 436,506

[22] Filed: May 8, 1995

Related U.S. Application Data

[63] Continuation of Ser. No. 322,029, Oct. 12, 1994, which is a continuation of Ser. No. 65,967, May 21, 1993, abandoned.

[51] Int. Cl.[6] ..................................................... A61K 7/075
[52] U.S. Cl. .................. 424/70.1; 424/70.31; 424/70.12; 424/70.13; 536/4.1; 536/6.0
[58] Field of Search ...................... 424/70.1, 71; 536/4.1, 536/6

[56] References Cited

U.S. PATENT DOCUMENTS

| | | | |
|---|---|---|---|
| 4,668,422 | 5/1987 | Malik et al. | 252/174.17 |
| 5,059,414 | 10/1991 | Dallal et al. | 424/70 |
| 5,120,531 | 6/1992 | Wells et al. | 424/70 |
| 5,120,532 | 6/1992 | Wells et al. | 424/70 |
| 5,223,179 | 6/1993 | Connor et al. | 252/548 |

*Primary Examiner*—Shelley A. Dodson
*Attorney, Agent, or Firm*—Wayne C. Jaeschke; John E. Drach; Henry E. Millson, Jr.

[57] ABSTRACT

Foaming shampoo compositions which contain no anionic surfactant and are mild to the skin and eyes are comprised of alkyl polyglycosides, betaines, and polymeric slip agents.

18 Claims, No Drawings

MILD SHAMPOO COMPOSITION

This application is a continuation of application Ser. No. 08/322,029 filed on Oct. 12, 1994, which is a continuation of Ser. No. 08/065,967 filed on May 21, 1993 now abandoned.

BACKGROUND OF THE INVENTION

1. Field of the Invention

This invention relates to non-anionic, foaming shampoo compositions which are mild to the skin and eyes and are comprised of alkyl polyglycosides, betaines, and polymeric slip agents.

2. Description of the Related Art

Shampoo formulations which contain anionic surfactants can be irritating to the skin and eyes. In addition, the presence of the anionic surfactants limits the types of additives such as cationic conditioners and hair colorants which can also be added to the shampoo formulations. The absence of anionic surfactants also permits more efficient deposition of such components as anti-dandruff additives on the hair. The shampoo formulations according to the invention are free of anionic surfactants and are, therefore, able to be formulated with cationic materials and other types of additives that are precluded by the presence of anionic surfactants.

SUMMARY OF THE INVENTION

It has been discovered that shampoo formulations containing alkyl polyglycosides, betaines, amine oxides, and polymeric slip agents exhibit excellent foaming properties and are mild to the skin and eyes. The shampoo formulations according to the invention exhibit good foaming characteristics in the absence of anionic surfactants while also providing a lubricous-feeling lather.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about."

Applicants have made the surprising discovery that shampoo formulations containing: (a) water; (b) from 5% to 20% by weight of a compound of the formula I $$R^1O(G)_n \qquad (I)$$

wherein $R^1$ is a monovalent organic radical containing from about one to about 30 carbon atoms; G represents a moiety derived from a reducing saccharide containing from 5 or 6 atoms; n is a number having an average value from 1 to about 6; (c) from 1% to 5% by weight of a betaine of the formula II

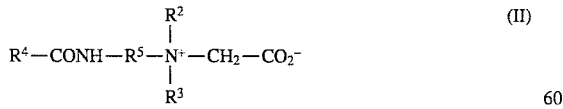

wherein $R^4$ is an alkyl or alkenyl group having from 7 to 21 carbon atoms and $R^5$ is alkylene group having from 2 or 3 carbon atoms; each of $R^2$ and $R^3$ is independently an alkyl group having from 1 to 4 carbon atoms; (d) from 2% to 5% by weight of an amine oxide of the formula (III)

$$R^6R^7R^8NO \qquad (III)$$

wherein each of $R^6$, $R^7$ and $R^8$ is independently an alkyl group having from 1 to 22 carbon atoms; (e) from 0.1% to 0.5% by weight of a polymeric material selected form the group consisting of: (1) water soluble polyacrylate, (2) a water soluble polymethacrylate, (3) carboxymethyl cellulose, (4) hydroxyethyl cellulose, (5) a water soluble silicone (6) polyethylene glycol, and (7) quaternized guar gum are mild to the skin and eyes and exhibit foaming properties characteristic of shampoos which contain anionic surfactants.

The alkyl polyglycosides which can be used in the shampoo compositions according to the invention have the formula I and are commercially available as APG®, Glucopon™, or Plantaren™ surfactants from Henkel Corporation, Ambler, PA., 19002. Examples of such surfactants include but are not limited to:

1. APG® 225—an alkylpolyglycoside in which the alkyl group contains 8 to 10 carbon atoms.
2. APG® 425—an alkyl polyglycoside in which the alkyl group contains 8 to 16 carbon atoms.
3. APG® 625—an alkyl polyglycoside in which the alkyl groups contains 12 to 16 carbon atoms.
4. APG® 300—an alkyl polyglycoside substantially the same as the 325 product above but having a different average degree of polymerization.
5. Glucopon™ 600—an alkylpolyglycoside substantially the same as the 625 product above but having a different average degree of polymerization.
6. Plantaren™ 2000—a $C_{8-16}$ alkyl polyglycoside having an average degree of polymerization of 1.4.
7. Plantare™ 1300—a $C_{12-16}$ alkyl polyglycoside having an average degree of polymerization of 1.6.
8. Plantaren™ 1200—a $C_{12-16}$ alkyl polyglycoside having an average degree of polymerization of 1.4. Other examples include alkyl polyglycoside surfactant compositions which are comprised of mixtures of compounds of formula I wherein G represents a moiety derived from a reducing saccharide containing 5 or 6 carbon atoms; n is a number from 1.8 to 3; and $R^1$ is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in copending application Ser. No. 07/810,588, filed on 12/19/91, the entire contents of which are incorporated herein by reference. The amount of the alkyl polyglycoside which can be used in the shampoo compositions according to the invention can range from 5 to 20% by weight, preferably from 10% to 15% by weight.

The betaines which can be used in the composition according to the invention are those of the formula II. The preferred betaines of the formula II are Velvetex® BK- 35, which is a $C_{12-18}$ cocoamidopropyl betaine and Velvetex® BA-35, which is a $C_{8-18}$ a cocoamidopropyl betaine. Both Velvetex® BK-35 and Velvetex® BA-35 surfactants are trademark products of Henkel Corporation, Ambler, Pa., 19002. The amount of betaine which can be used in the shampoo compositions according to the invention can range from 1 to 5% by weight, preferably from 2% to 4% by weight.

The amine oxides which be used in the composition according to the invention are those of the formula III. The preferred amine oxides include Standamox™ LAO-30 surfactant, which is a lauramine oxide and Standamox™ O1 surfactant, which is a oleamine oxide, both of which are trademark products of Henkel Corporation, Ambler, PA, 19002. The amount of amine oxide which can be used in the shampoo compositions according to the invention can range from 1 to 5% by weight, preferably from 2% to 4% by weight.

The polymeric materials which can be used as slip agents in the compositions according to the invention are polymers selected form the group consisting of: (1) a water soluble polyacrylate, preferably acrylamidomethylpropane sulfonic acid, commercially available as Cosmedia® Polymer HSP-1180, a trademark product of Henkel Corporation, Ambler, PA.; (2) a water soluble polymethacrylate, (3) carboxymethyl cellulose; (4) hydroxyethyl cellulose; (5) a water soluble silicone; (6) polyethylene glycol having a molecular weight of from about 200,000 to about 3,000,000 and (7) quaternized guar gum. Preferred water soluble polymers include Silicone Copolymer F-754, which is dimethicone copolyol, a trademark product of Wacker Silicones Corp., Adrian, Mich. and Polyox® WSRN 60K, which is a polyethylene glycol having a molecular weight of about 1,980,000, a trademark product Union Carbide Corporation, Danbury, Conn., and Hicare® 133, a trademark product of Rhone-Poulenc, which is poly(3-(methacrylamido)propyltrimethylammonium chloride. The amount of water soluble polymer which can be used in the shampoo compositions according to the invention can range from 0.1 to 0.5% by weight, preferably from 0.2% to 0.4%.

Optional ingredients which can also be added to the shampoo formulations according to the invention include amphoteric surfactants, pearlizing agents such as Euperlan™ 1000 pearlizing surfactant, a trademark product of Henkel Corporation, conditioners, anti-dandruff additives, hair colorants, sun screens, and refatting agents.

The following examples are meant to illustrate but not to limit the invention.

EXAMPLE 1

Clear Non-anionic Shampoo

To an appropriately sized vessel equipped with agitation was charged with 22.4 parts water, 30 parts Plantaren™ 2000 surfactant (50% active), 8.0 parts Velvetex™ BK-35 surfactant (30% active), 20 parts Deriphat™ 160C (the monosodium salt of laurimiodipropionate), 8 parts Standamox™ LAO-30, 8.0 parts Standamox™ O1, 0.50 parts Silicone Copolymer F-754, 3.0 parts PEG-6000 distearate, and 0.10 parts Kathon™ CG preservative, a trademark product of Rohm & Haas, Co, Phila., Pa. The agitation was continued after all the ingredients were added and the pH was adjusted to 6.0–6.5 with 50% aqueous citric acid. The agitation was continued until the mixture in the vessel was homogenous.

EXAMPLE 2

Pearlized Non-anionic Shampoo

To an appropriately sized vessel with agitation was charged with 22.4 parts water, 30 parts Plantaren™ 2000 surfactant, 8.0 parts Velvetex™ BK-35 surfactant, 20 parts Deriphat™ 160C, 8 parts Standamox™ LAO-30, 3.0 parts Euperlan™ 1000 pearlizing surfactant, 0.50 parts Silicone Copolymer F-754, 2.0 parts PEG-6000 distearate, 8 parts of a 2% aqueous Polyox™ solution, and 0.10 parts Kathon™ CG preservative. The agitation was continued after all the ingredients were added and the pH was adjusted to 6.0–6.5 with 50% aqueous citric acid. The agitation was continued until the mixture in the vessel was homogenous.

What is claimed is:

1. A shampoo composition comprising: (a) water; (b) from about 5% to about 20% by weight of a compound of the formula I $$R^1O(G)_n \qquad (I)$$

wherein $R^1$ is a monovalent organic radical containing from about one to about 30 carbon atoms; G represents a moiety derived from a reducing saccharide containing 5 or 6 carbon atoms; n is a number having an average value from 1 to about 6; (c) from 1% to 5% by weight of a betaine of the formula II $$R^4-CONH-R^5-\underset{\underset{R^3}{|}}{\overset{\overset{R^2}{|}}{N^+}}-CH_2-CO_2^- \qquad (II)$$

wherein $R^4$ is an alkyl or alkenyl group having from 7 to 21 carbon atoms and $R^5$ is an alkylene group having from 2 or 3 carbon atoms; each of $R^2$ and $R^3$ is independently an alkyl group having from 1 to 4 carbon atoms; (d) from 2% to 5% by weight of an amine oxide of the formula (III)

$$R^6R^7R^8NO \qquad (III)$$

wherein each of $R^6$, $R^7$ and $R^8$ is independently an alkyl group having from 1 to 22 carbon atoms; (e) from 0.1% to 0.5% by weight of a polymeric material selected form the group consisting of: (1) a water soluble silicone (2) polyethylene glycol having a molecular weight of from about 200,000 to about 3,000,000, and (3) quaternized guar gum.

2. The composition of claim 1 wherein compound of the formula I is a $C_{8-16}$ alkyl polyglycoside having an average degree of polymerization of 1.4.

3. The composition of claim 1 wherein said compound of the formula I is present in an amount of from about 10% to about 15% by weight.

4. The composition of claim 1 wherein said compound of the formula II is present in an amount of from about 2% to about 4% by weight.

5. The composition of claim 1 wherein said compound of the formula III is present in an amount of from about 2% to about 4% by weight.

6. The composition of claim 1 wherein said compound of the formula II is a $C_{12-18}$ is cocoamidopropyl betaine or a $C_{8-18}$ is cocoamidopropyl betaine.

7. The composition of claim 1 wherein said polymeric material is present in an amount of from about 0.2% to about 0.4% by weight.

8. A composition comprising: (a) water; (b) from about 15% to about 20% by weight of a $C_{8-18}$ alkyl polyglycoside having an average degree of polymerization of 1.4; (c) from about 2% to about 4% by weight of a $C_{8-18}$ cocoamidopropyl betaine; (d) from about 2% to about 4% by weight of a lauramine oxide or an oleamine oxide; and from about 0.2% to about 0.4% by weight of polyethylene glycol having a molecular weight of from about 200,000 to about 3,000,000.

9. A composition comprising: (a) water; (b) from about 15% to about 20% by weight of a $C_{8-16}$ alkyl polyglycoside having an average degree of polymerization of 1.4; (c) from about 2% to about 4% by weight of a $C_{12-18}$ cocoamidopropyl betaine; (d) from about 2% to about 4% by weight of a lauramine oxide or an oleamine oxide; and from about 0.2% to about 0.4% by weight of dimethicone copolyol.

10. A process for shampooing hair comprising adding to hair a shampoo effective quantity of a shampoo composition comprising: (a) water; (b) from about 5% to about 20% by weight of a compound of the formula I

$$R^1O(G)_n \qquad (I)$$

wherein $R^1$ is a monovalent organic radical containing from about one to about 30 carbon atoms; G represents a moiety derived from a reducing saccharide containing 5 or 6 carbon atoms; n is a number having an average value from 1 to about 6; (c) from 1% to 5% by weight of a betaine of the formula II

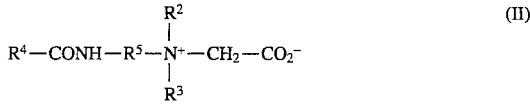

$$R^4-CONH-R^5-\overset{\overset{\displaystyle R^2}{|}}{\underset{\underset{\displaystyle R^3}{|}}{N^+}}-CH_2-CO_2^- \qquad (II)$$

wherein $R^4$ is an alkyl or alkenyl group having from 7 to 21 carbon atoms and $R^5$ is alkylene group having from 2 or 3 carbon atoms; each of $R^2$ and $R^3$ is independently an alkyl group having from 1 to 4 carbon atoms; (d) from 2% to 5% by weight of an amine oxide of the formula (III)

$$R^6R^7R^8NO \qquad (III)$$

wherein each of $R^6$, $R^7$ and $R^8$ is independently an alkyl group having from 1 to 22 carbon atoms; (e) from 0.1% to 0.5% by weight of a polymeric material selected form the group consisting of: (1) water soluble polyacrylate, (2) a water soluble polymethacrylate, (3) carboxymethyl cellulose, (4) hydroxyethyl cellulose, (5) a water soluble silicone (6) polyethylene glycol, and (7) quaternized guar gum.

11. The process of claim 10 wherein in said shampoo composition the compound of the formula i is a $C_{8-18}$ alkyl polyglycoside having an average degree of polymerization of 1.4.

12. The process of claim 10 wherein in said shampoo composition the compound of the formula I is present in an amount of from about 10% to about 15% by weight.

13. The process of claim 10 wherein in said shampoo composition the compound of the formula II is present in an amount of from about .2% to about 4% by weight.

14. The process of claim 10 wherein in said shampoo composition the compound of the formula III is present in an amount of from about 2% to about 4% by weight.

15. The process of claim 10 wherein in said shampoo composition the compound of the formula II is a $C_{12-18}$ cocoamidopropyl betaine or a $C_{8-18}$ is cocoamidopropyl betaine.

16. The process of claim 10 wherein in said shampoo composition the polymeric material is present in an amount of from about 0.2% to about 0.4% by weight.

17. The process of claim 10 wherein said shampoo composition comprises: (a) water; (b) from about 15% to about 20% by weight of a $C_{8-18}$ alkyl polyglycoside having an average degree of polymerization of 1.4; (c) from about 2% to about 4% by weight of a $C_{8-18}$ cocoamidopropyl betaine; (d) from about 2% to about 4% by weight of a lauramine oxide or an oleamine oxide; and from about 0.2% to about 0.4% by weight of polyethylene glycol having a molecular weight of from about 200,000 to about 3,000,000.

18. The process of claim 10 wherein said shampoo composition comprises: (a) water; (b) from about 15%, to about 20% by weight of a $C_{8-18}$ alkyl polyglycoside having an average degree of polymerization of 1.4; (c) from about 2% to about 4% by weight of a $C_{12-18}$ cocoamidopropyl betaine; (d) from about 2% to about 4% by weight of a lauramine oxide or an oleamine oxide; and from about 0.2% to about 0.4% by weight of dimethicone copolyol,

\* \* \* \* \*